United States Patent [19]

Broadwin et al.

[11] 4,136,700
[45] Jan. 30, 1979

[54] NEUROSONIC ASPIRATOR

[75] Inventors: Alan Broadwin, Brooklyn, N.Y.; Steven N. Weiss, Laguna Niguel, Calif.; Stanley H. Enker, Lawrence, N.Y.

[73] Assignee: Cavitron Corporation, New York, N.Y.

[21] Appl. No.: 696,321

[22] Filed: Jun. 14, 1976

Related U.S. Application Data

[62] Division of Ser. No. 555,474, Mar. 5, 1975, Pat. No. 4,016,882.

[51] Int. Cl.² ............................................. A61B 17/32
[52] U.S. Cl. ................................. 128/305; 128/24 A; 128/276
[58] Field of Search .............. 128/305, 303.14, 303 C, 128/24 A, 276

[56] References Cited
U.S. PATENT DOCUMENTS

| | | | |
|---|---|---|---|
| 2,990,616 | 7/1961 | Balamuth et al. | 128/303 C UX |
| 3,076,904 | 2/1963 | Kleesattel et al. | 128/303 C UX |
| 3,375,583 | 4/1968 | Blank et al. | 128/303 C UX |
| 3,526,219 | 9/1970 | Balamuth | 128/24 A |
| 3,857,387 | 12/1974 | Shock | 128/303 C UX |
| 3,902,495 | 9/1975 | Weiss et al. | 128/303 C UX |

*Primary Examiner*—Robert W. Michell
*Assistant Examiner*—Michael H. Thaler
*Attorney, Agent, or Firm*—Robert M. Skolnik; William R. Evans

[57] ABSTRACT

Apparatus for use in surgically removing tumorous neurological tissue comprises a handpiece in which a tool tip vibrating transversely to its long axis in the ultrasonic range, is mounted an irrigation fluid outlet for introducing fluid adjacent the tool tip to flush the operative site, and a fluid inlet adjacent the tool tip for withdrawing a fluid mixture from the site.

12 Claims, 4 Drawing Figures

U.S. Patent  Jan. 30, 1979  4,136,700
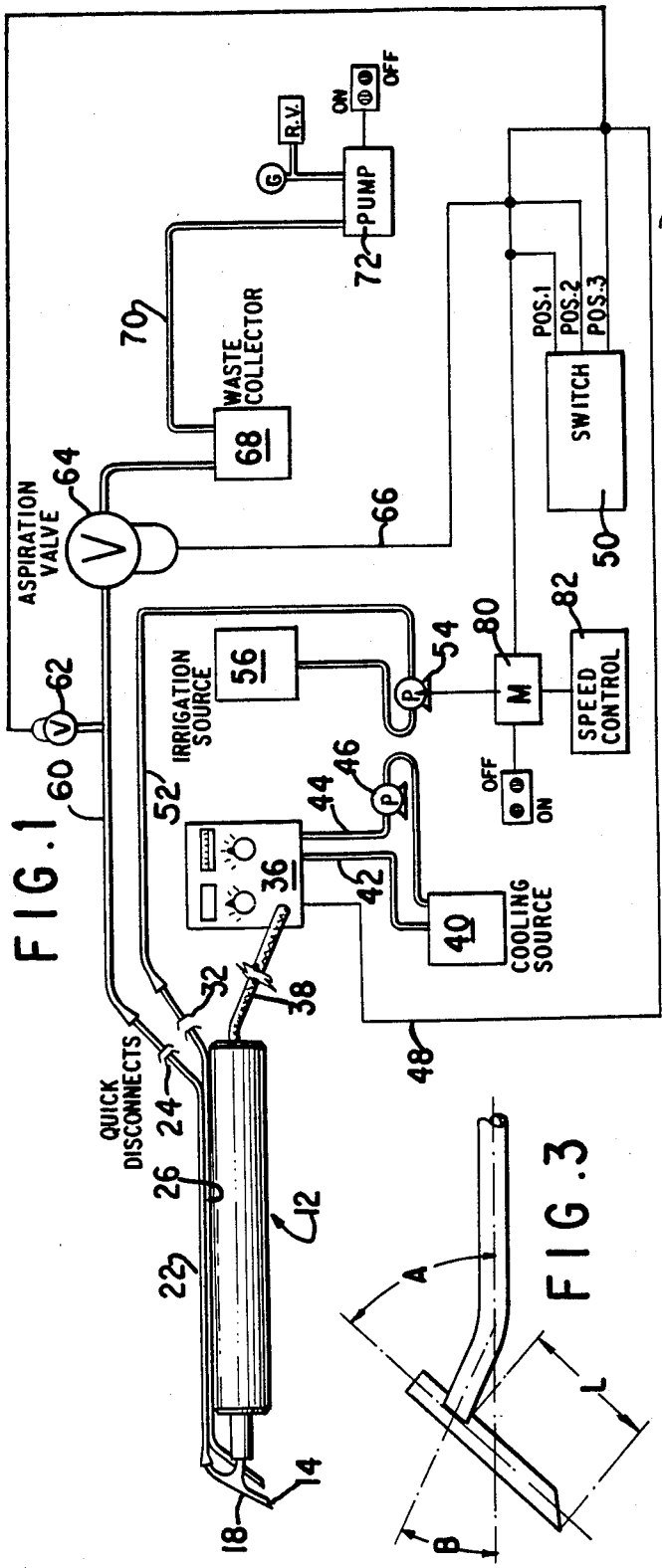
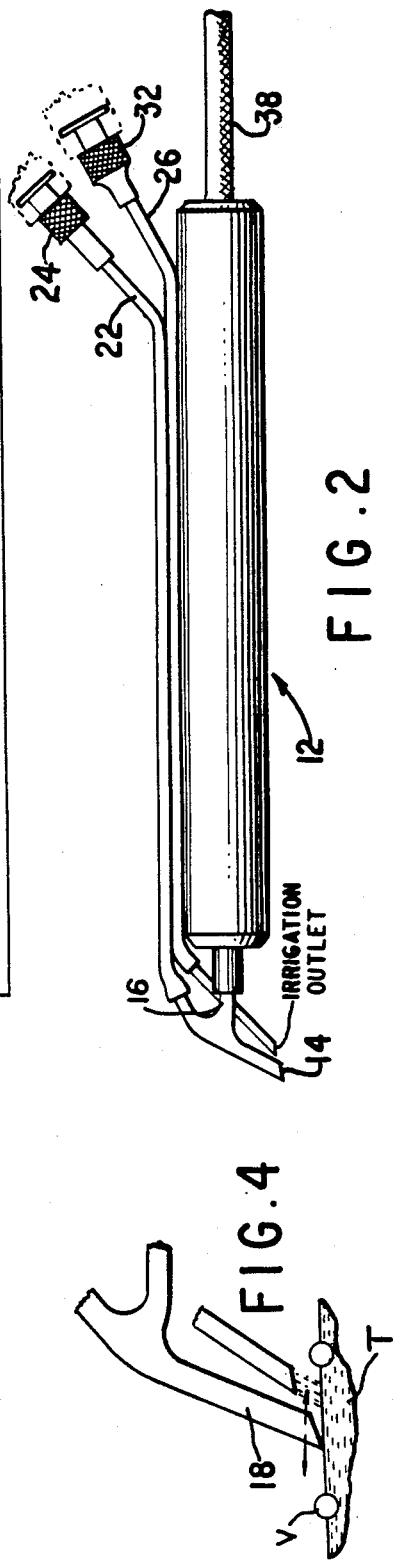

NEUROSONIC ASPIRATOR

This is a division, of application Ser. No. 555,474, filed Mar. 5, 1975, now U.S. Pat. No. 4,016,882.

BACKGROUND OF THE INVENTION

This invention relates to an apparatus and method for performing surgery. More particularly this invention relates to apparatus for ultrasonically removing neurological type organic tissues in a manner which limits destruction of adjacent tissue. In neurological surgery as for instance the removal of benign tumorous tissues, the present technique is to evacuate the central volume of the tumor by using an electrosurgical loop or a sharp spooned curette after which the remaining tumor shell is dissected from the healthy tissue. The problem with this procedure is the fact that cutting is performed forward of the visible tissue which makes it virtually impossible for the surgeon to see what is being cut. Therefore the cutting edge may penetrate blood vessels within the area of the tumor causing severe bleeding and further limiting visibility in the operative site. Of greater danger is the possibility of damage to a major blood vessel or a nerve such as the carotid artery or the optic nerve, either of which represents severe trauma to the patient. It therefore would be advantageous to provide some other surgical way of cutting and removing neurological tissue which does not present or minimize such problems.

Ultrasonically vibrated surgical instruments are known and are being employed in certain types of specialized surgery, particularly in dentistry to clean tooth surfaces, and in the removal of cataracts. Illustrative of the former is U.S. Pat. No. 2,990,616 issued July 4, 1961 for Ultrasonic Cutting Tool, while instruments for accomplishing the latter type of surgery are illustrated by U.S. Pat. No. 3,589,363 issued June 29, 1971 to A. Banko and C. D. Kelman for a Material Removal Apparatus and Method Employing High Frequency Vibrations.

Prior art apparatus such as that disclosed by the aforesaid Banko et al U.S. Pat. No. 3,589,363 is intended for ultrasonic aspiration of tissues such as cataracts and has been examined and found to be effective therefor. The apparatus according to the aforementioned Banko et al Patent employs a handpiece and has a hollow tip which is longitudinally vibrated and designed for precise removal of small quantities of non-vascularized tissue, such as that in a cataract lens. It relies on the fact that cataract surgery removes material from within an enclosed operative site so that the application of suction through the hollow center of the tip staying in a relatively stationary position is not a problem. Indeed, it is important in cataract surgery because of the possibility of damage to other coextensive tissue structures.

Brain or neurological and other soft tissues present a different set of conditions than those encountered in cataract surgery. Since relatively larger masses of tissue are involved here, including the requirement for speedy and precise removal of undesired tissue (with minimum trauma or damage to adjacent healthy tissue) apparatus suitable for cataract removal is generally ineffective.

Further, (senile) cataract tissue is relatively hard, brittle and (possibly) calcified in contrast to other soft tissues such as neurological (brain), liver, lung tissue, etc. for example. Apparently the more elastic and fibrous a tissue, such as a soft tissue as compared to a cataract tissue, the greater difficulty there exists in fragmenting and aspirating it according to the methods and apparatus disclosed by Banko et al.

SUMMARY OF THE INVENTION

We have invented apparatus for performing neurosurgery, comprising, in combination, an ultrasonically vibrated tool having a longitudinal axis extending from one end which vibrates substantially entirely transversely to the longitudinal axis and a connecting member extending from the tool for connecting it to a device for ultrasonically vibrating the tool. Preferably, a fluid supply for introducing fluid into the area adjacent to the tool and an aspirator for removing material from the area adjacent the tool are also provided. Preferably the tool also comprises a handpiece, a vibration transducer mounted in the handpiece, and a tool tip connected to the transducer. The tool vibrates in a plane transverse to its long axis for surgically fragmenting tissue exposed to view and swept with the ultrasonically vibrating tool, said tool vibrating transversely to the tool axis to remove the tissue layer by layer.

Accordingly, it is an object of the present invention to provide novel apparatus for surgically removing neurological tissue;

Another object of this invention is to provide for ultrasonic fragmentation of undesired tissue while limiting damage to resilient tissue structures;

Still another object is to provide method and apparatus which limits loss of blood;

Yet another object of this invention is to provide a novel and unique surgical procedure for removal of benign tumors of the brain and spinal cord;

A particular object of this invention is to provide apparatus for micro surgically fragmenting neurological tissue and simultaneously aspirating same;

Yet another object of this invention is to provide apparatus which removes tissue layer by layer;

Another object is to provide apparatus and method which allow visual monitoring of tissue as it is removed;

Still another object of this invention is to provide apparatus and method for increasing the speed of a surgical procedure;

Other objects and advantages of the apparatus and method of this invention will be apparent from the description of the drawings and preferred embodiment which follows.

BRIEF DESCRIPTION OF THE DRAWINGS

FIG. 1 is a system drawing of the apparatus according to the present invention;

FIG. 2 is a more detailed drawing of the anterior end of the handpiece of the present invention;

FIG. 3 is a detailed view of a preferred embodiment of the tool tip according to the pressent invention; and FIG. 4 is a view of the method fragmentation according to the present invention.

DESCRIPTION OF THE PREFERRED EMBODIMENTS

This invention is particularly applicable to use in neurosurgery. To provide an effective instrument for removing neurological tumorous tissue we have invented an ultrasonically vibrated instrument with which a surgeon can effectively remove tumorous tissue by disintegrating or comminuting such tissue while keeping the effects of the instrument continually under observation, irrigating the operative area and withdrawing the comminuted tissue therefrom. More specifically surgeons in operating on neurological tissue, i.e., tumorous brain tissue, employ either a scalpel or an electrosurgical instrument to excise the body of the tumor and then remove the shell by dissection. Since only the outer surface of the tumor is generally visible, the surgeon has to depend upon his experience, apparent knowledge of the tumor size and its relation to surrounding structures to limit the depth of penetration, excision and tissue removal. As the tumor may be adjacent critical structures such as principal blood vessels and nerves, not to mention relatively healthy brain tissue and minor blood vessels, it is difficult to prevent inadvertant damage to such structures from direct cutting, pulling, ripping and tugging, and also from heat generated by an electrosurgical tool if such is employed. Our apparatus and method employs an instrument which readily disintegrates the tumorous neurological tissue, yet does not readily damage vascular and other adjacent tissue. Furthermore, it allows the surgeon to directly view the tissue being excised and does not generate sufficient heat to damage any adjacent tissue.

The instrument according to this invention is illustrated in FIG. 1 of the drawing. The apparatus comprises an ultrasonic handpiece 12 on which an ultrasonically vibrated tool tip 14 is located at its anterior end. The handpiece 12 is a tubularly shaped device in which an ultrasonic vibration transducer is enclosed such as that shown by U.S. Pat. No. 3,589,363. Such ultrasonic transducers are well known in the art and are incorporated herein by reference to the aforementioned patent. Typically, a generator powered by conventional current generates a high frequency current which induces a vibratory excitation in the transducer. Conventionally a coolant fluid is introduced into the handpiece adjacent the spaces occupied by the transducer to furnish cooling to the components of the transducer.

The tool tip 14 is connected to the handpiece 12 along its long side by brazing or otherwise mechanically attaching the tip to a connecting member 16 which is in turn dynamically coupled to the ultrasonic transducer in the handpiece. As illustrated the tool tip 14 is attached to the connecting member at an oblique angle to the longitudinal axis of the connecting member which acts to effect a vibratory motion a the end of the tip that is transverse to a longitudinal axis of the tool tip extending from one end thereof. Such transverse vibratory motion as shown in FIG. 4 of the drawings is an important feature of this invention as other modes of vibration, vis longitudinal motion, do not operate effectively on the tumorous neurological tissue. Thus we have discovered that a transverse vibration in the range of from about 20 KHz to about 40 KHz with a vibratory amplitude of from about 0.0005 inches to about 0.005 inches peak to peak is effective in achieving the above objective of this invention. A vibration in the range of from about 25 KHz is preferred for practicing this procedure.

More specifically an effective tool tip and connecting member combination is shown in FIG. 3 of the drawings and structured as follows: The tool tip is a hollow metal tube having an internal diameter between about 0.042 and about 0.093 inches, a wall thickness of from about 0.005 to 0.02 inches, and a length (L) measured from the connecting member to the tip end of from about 0.05 to 1.0 inches. The angle (A) formed by the major axis of the connecting member and the tool tip is from about 0 degrees to about 60 degrees. While the connecting member may be itself bent for a short distance from its point of attachment to the tip from about 0° to about 20° (Angle B). The bevel at the tool tip end is between 0° and 45° relative to a perpendicular to the longitudinal axis of the tool tip whereby, together, the plane of the end of the tool tip is at an angle of between 30° and 90° to the longitudinal axis of the connecting member 16. Such a configuration induces flexural, i.e., transverse vibration in the tool tip with a magnification of from about 3:1 through 5:1.

We have found such an ultrasonically vibrated tool to be quite effective for surgical removal of relatively large masses of tissue which are often highly vascular such as brain tissue, and liver tissue. The appropriate and effective type of motion of the instrument as applied to the tissue surfaces is a sweeping motion with the tip vibrating across the swept tissue surfaces as shown in FIG. 4. Such motion with the tip ultrasonically vibrating in a transverse or flexural motion to its longer axis, fragments tissue at a rapid enough rate to readily remove tissue generally the subject of such neurological surgery such as removal of benign tumors from the brain or other nerve areas, or even for removal of undesired tissue from the liver or lungs. It has been found that the transversely vibrated tip surprisingly glides over blood vessels. It is hypothesized that blood vessels, or any other "resilient body" tissues are not affected by this type of ultrasonic vibrating tip. This applies also to the capsule that encloses a benign tumor, and to such tissue structures as the dura, i.e., the sack which encloses the entire brain mass in the skull. The motion of the ultrasonically vibrating tips for surgery is typically a half a thousandth, i.e., 0.0005 to five thousandths, (0.005) peak to peak excursion. Thus for such tip motions with a maximum unload peak to peak excursion of five thousandths of an inch when applied to arterial or venous material or encapsulating membrane which is highly elastic, it is believed that these tissues will stretch and give much more than five thousandths of an inch before they will fracture or sever.

In cataract surgery the fact that tissues to be removed have a fairly low elastic limit and will therefore exhibit a brittle type of fracture for relatively low or small stains allows fragmentation to occur satisfactorily with a device such as disclosed in the aforementioned U.S. Pat. No. 3,589,363. However, the longitudinal vibration of the cataract surgical tip tends to make it prone to penetrate and/or puncture elastic tissue such as a blood vessel wall in contrast to the transverse or flexural motion of the present apparatus and procedure.

Referring to FIGS. 1 and 2 the tool tip 14 is a hollow metal tube 18 with its upper end 20 attached to fluid withdrawal tubing 22 which tubing extends the length of the handpiece to quick disconnect 24. Also mounted on the handpiece is an irrigation tube 26 connected at its forward end to an irrigation nozzle 28 having its nozzle opening directed at the area adjacent to the tool tip. Another quick disconnect 32 is located at the other end of the irrigation tube. Irrigation, i.e., supplying of a sterile fluid to the operative site via irrigation nozzle 28, provides a suitable medium for suspending tumorous tissue which has been excised by the application of the ultrasonically vibrated tip. Irrigation further cools and flushes the operative site to an extent. By suspending the disintegrated tissue in the irrigation fluid, the suspension of tissue, the fluid and blood sometimes referred to as a fluid mixture herein, can be continually and readily withdrawn from the operative site by aspiration through the hollow tool tip 14. The surgeon can during the procedure turn off the ultrasonic vibration and use the aspiration to clear the operative site of fluid before proceeding to further excise material by again applying ultrasonic vibration to the tip. Irrigation of the site is also readily controllable by the surgeon by use of the present apparatus by use of the various controls which are described hereinafter.

Connected to the rear of the handpiece is a power cord 38 normally comprising a four wire line having three conductors not shown and a grounded shield. The power cord is connected at its other end to an ultrasonic generator 36. The ultrasonic generator 36 is an electrical unit capable of generating a high frequency alternating current; suitable frequencies being from 20 KHz to about 40 KHz, which current is used to drive a transducer in the handpiece. Also enclosed in the power cord are two coolant conduits, one which acts to carry cooling water to the interior of the handpiece to thereby cool the ultrasonic vibrator, and a return conduit to return the heated coolant to its source. The coolant is supplied from a cooling source 40 connected by a pipe 42 to the generator and by a second coolant supply pipe 44 to a coolant pump which in turn pumps the coolant to the generator for supply to the handpiece. Power is supplied to the generator through line 48 and controlled by footswitch 50.

An irrigation line 52 is connected by the quick disconnect 32 to the irrigation tube 26 on the handpiece. The irrigation line is preferably in the form of flexible tubing allowing use of a pump such as pump 54 for pumping sterlie irrigation fluid from an irrigation solution. Pumping irrigation fluid to the area of the tool tip and the operative site provides sufficient fluid to allow the tissue disintegrated by the ultrasonic vibration to be suspended by the fluid and to wash away such tissue thereby keeping the operative site relatively clear for viewing by the surgeon.

The other disconnect is connected to an aspiration line 60 for withdrawing the mixture of fluid, disintegrated body tissues and other matters from the operative site. A vent valve 62 connected to the aspiration line opens the aspiration line to atmosphere when switch 50 is suitably actuated to quickly release tissue from the tool tip opening. Also mounted in the aspiration line 60 is a switch controlled shutoff aspiration valve 64 which is controlled by the footswitch 50 via cable 66. From the shutoff valve the aspiration line feeds to a waste collector 68 which collector is a sealed container having the aspiration line leading into it and a pump line 70 leading out. The pump line is connected to a vacuum pump 72 having suitable controller, i.e., a gage, a relief valve and an on-off switch.

Preferably the irrigation line 52 is a length of plastic tubing such high quality laboratory tubing which is connected to the pump 54 of the type having a roller, not shown, which peristaltically employs the elastic tubing of the irrigation line. Source 56 contains a sterile or other desirable medicinal solution. The pump 54 is powered by a motor 80 of conventional type whose speed is controlled as desired by a suitable speed control 82 both to which are well known in the art. The electrical power is supplied from a conventional source as is all power in the system and is controlled by the surgeon by means of the switch 50.

In use the surgeon has full control over the handpiece and the irrigation, aspiration system. By use of the switch 50 in its various positions he can apply ultrasonic energy to the tool tip and simultaneously aspirate and irrigate the operative site. He can also apply untrasonic energy to the handpiece without irrigation as desired, or he can apply either aspiration or irrigation without applying the ultrasonic energy.

FIG. 2 of the drawings shows the handpiece. The handpiece 12 comprises an outside tubular housing enclosing an ultrasonic transducer for converting the electronic signal from the generator 36 to ultrasonic vibration of the transducer which transmits such ultrasonic vibration to the tool tip, through the connecting member 16. The connecting member 16 is vibrated substantially along its long axis, that is it is vibrated longitudinally rather than transversly. This longitudinal vibration is transferred to the tool tip 14 which is brazed to the end of the connecting member at an angle, preferably between about 0 degrees and about 60 degrees and results in a transverse vibration being exhibited by the end of the tool tip. As stated previously such transverse vibration is an important feature of this invention as it has been found that longitudinal vibration is ineffective when applied to tumorous neurological tissue. It is understandably important that the disintegrating action of the ultrasonically vibrated tool be as rapid as possible, since "time under the knife" should be as short as possible for the patient and the surgeon. The disintegrating action should be as efficient as possible to terms of energy dissipation at the tool tip.

It has been found that a hollow tool tip having a length of about one and one-half inches with an ID of about 0.063 inches, a wall thickness of about 0.01 inches, and a tip end cut at a 30 degree angle is preferred for such surgery. The end farthest away from the tip end may be bent so as to connect the tubing lying adjacent the handpiece. Size understandably is important since it does effect vibrational characteristics of the tip itself and the internal diameter of the hollow tube through the tip effects the removal rate (aspiration) from the operative site and the size of tissue particles that can be aspirated.

Other instruments can be incorporated in the principal apparatus of this invention. For instance light can be supplied directly to the site by use of fiber optics, the optical tube being disposed adjacent the handpiece and illuminating the area adjacent the tool tip. A coagulator for sealing several minor blood vessels can also be employed in conjunction with the present invention, such coagulators being well known.

Employing the present inventive apparatus, the surgeon opens the patients skull in the conventional manner and exposes the tumor. Once exposed, the ultrasonic tip is activated and irrigation and aspiration simultaneously activated. The surgeon then proceeds to apply the tip to the tissue surface continually disintegrating the tissue which is aspirated through the hollow tube of the tip. This is an important feature as it immediately removes fragmented tissue from the operative site preventing retention thereof in the patient post operatively and aspiration through the tool tip minimizes the area of tissue being subject to disintegration and aspiration at any one time as the fragmented tissue is withdrawn along with the aspirated fluid until the tumor is completely removed. During the course of the operation the surgeon may use the tip solely as an aspirator or irrigator.

Thus, procedurally the surgical method according to our invention comprises disintegrating tissue by contacting the same with an ultrasonically vibrated tool, which tool is vibrating transversely to the long axis of the tip and to the direction of contact and simultaneously aspirating, (i.e., withdrawing) the disintegrated tissue. The ultrasonically vibrating tool is swept back and forth over the external layer of tissue, contacting, disintegrating and aspirating the disintegrated layer thereby removing the tissue layer by layer. More specifically, the procedure comprises disintegrating neurological (brain) tissue by contacting the tissue with a tool vibrating transversely at a frequency of from about 20 KHz to about 40 KHz; and simultaneously irrigating the area adjacent the tool and aspirating the disintegrated tissue and irrigation fluid. Specifically, the frequency used is preferably about 25 KHz.

The present apparatus is preferably utilized according to the following procedure for the removal of an encapsulated benign tumor present either in the patient's brain or spinal column. The surgeon prepares the patient in the conventional manner wherein he removes a flap of the skull or spinal column vertebrae as the case may be, dissects the outer protective membrane with a scalpel and retracts the section of brain or spinal column to expose the tumor. The surgeon then makes an incision in the shell of the tumor using a scalpel allowing entry into the core thereof. The surgeon then applies the tool tip through the incision in the tumor membrane and applies ultrasonic excitation thereto to flexurally vibrate the tip transversely as he moves the tip over the core tissue to gently fragment the core tissue layer by layer. Minor blood vessels which are exposed and may be ruptured are coagulated with a conventional coagulator attachment (not shown). Simultaneously the core tissue of the tumor as it is fragmented layer by layer is aspirated through the tip's hollow tube. Once the bulk of the tumor core is removed, the surgeon then conventionally dissects away the remaining tumor shell, and completes the procedure. Irrigation is applied as required throughout the procedure. Briefly the aforesaid procedure can preferably be applied to various types of tumors, for example, olefactory groove meningiona, medial apheriod meningiona, acostic neurona, pituitary adenonas, cerebral tumors and spinal column tumors.

In all of the above applications, the apparatus according to the present invention will gently fragment the tumor (T) layer by layer and continuously irrigate the area while aspirating fragmented particles and allowing the surgeon to operate under direct vision. Vessels (V) within the tumor will be exposed and left basically intact as they are approached. The apparatus also enables the surgeon to coagulate small ruptured vessels significantly reducing bleeding, and then continue to proceed with the ultrasonic fragmentation to remove other tumorous tissue. Thus, the tumor is gradually reduced in size with minimum trauma to adjacent tissues. After the bulk of the tumor is removed, the tumor membrane is neatly dissected from good tissue with a scalpel. Advantageously the present invention enhances gentle removal of unwanted tissue, increases direct vision of the surgeon at the operative site, minimizes trauma to adjacent tissues, reduces blood loss during surgery and shortens the length of the procedure.

With reference to the surgical procedure according to the present invention, the following examples are given by way of illustration and not limitation.

EXAMPLE A

Experimental surgery was performed on a 56 year old male, who was suffering from loss of speech and general mental confusion. Presurgical diagnosis by angeograms had indicated a mass in the temporal lobe of the left side of the brain which was suspected to be either a metastatic tumor or an abscess. The surgical procedure commenced with a transcortical incision in the middle to lower temporal lobe on the left side. Probing revealed a large mass embedded one to two centimeters below the brain surface. The upper surface of this mass was exposed using conventional surgical procedures and apparatus, "white" matter clinging to the surface of the mass was removed by applying the aspirating ultrasonic vibrating tool tip to such matter. Extraction was accomplished by the surgeon gently tugging on the mass with forceps and then applying the ultrasonic vibrating tip in a sweeping motion at the juncture of the mass and tissues, which application definitely aided in extraction of the mass. Severed blood vessels ("bleeders") in the white matter were then coagulated electrosurgically, the bone and scalp flaps replaced and the site closed. The various modes; ultrasonic vibration of the tool tip; irrigation; coagulation; and aspiration were controlled by the surgeon through verbal command while the handpiece was fully controlled and manipulated by the surgeon. Pathological examination of tissue removed indicated it to be an abscess. As the mass was not of the type requiring fragmentation or disintegration for extraction, the ultrasonic vibrating and aspirating tip was employed only to separate the abscess from the normal brain tissue.

EXAMPLE B

Experimental surgery with the apparatus of this invention was performed on a 69 year old male suffering from partial facial paralysis and weakness in hands and arms. Presurgical diagnosis employing angeograms revealed a distinct mass in the right lateral frontal area of the brain and indicated the presence of a menigioma. Besides the apparatus according to the present invention (and employing handswitch controls, color coded tubing and a handpiece cable guide), a color video recording system was employed to monitor and record the surgical procedure.

Applying conventional surgical procedure, the brain was exposed to reveal a benign tumor adherent to the dura. The surgeon attempted to open the membrane with the ultrasonically vibrated tool. The membrane was finally torn by repeated scoring of its surface with the tip. Tearing of the membrane is thus believed to be more attributable to physical abrasion rather than ultrasonic fragmentation.

The incision in the membrane exposed an extremely and unusually thick wall, measuring in portions more than three millimeters. Once access was gained to the "fleshy" body of the tumor of the ultrasonic tip nicely fragmented and aspirated the core tissue of the tumor. The tumor, approximately the size of a hydrated prune, was composed in about half its bulk of the resilient membrane. The core, while fleshy, was not large or highly vascular. Video recording showed that the core was rapidly fragmented and swept out by the ultrasonic aspirating tip without major blood vessel damage. Vascular tissue damage and blood loss during the operation was much less than anticipated. During this procedure an operator soaked the handpiece in a cup provided on a sterile tray whenever the handpiece was not in use. Clogging of the hollow tip and aspiration line with clotted blood was thus avoided.

In summary, the excision of the tumor proceeded with the dissection of the membrane from normal brain tissue, a task made difficult by the highly adherent and tough wall. Several times additional "pockets" of tissue were uncovered and, in one instance, unusual tissue near the brain surface adjacent to the tumor was removed for pathological examination. The surgeon felt that this tissue might have been the agent for a spreading growth. The ultrasonic handpiece was not used for membrane separation.

Following removal of the meningioma, examination showed a clear barrier of the brain tissue at the base of the cavity formerly occupied by the tumor. As clean excision is difficult to obtain by other (non-sonic) prior art methods this desirable result was attributed to the use of ultrasonic fragmentation.

The above experimental procedures described in Examples A and B were preformed with apparatus according to this invention the following preferred operational parameters. The frequency generated in the ultrasonic range is about 25 KHz employing an ultrasonic tool tip having a length of about 0.687 inches from the point of attachment to the connecting member, an outside diameter of about 0.082 inches and an inside diameter of about 0.062 inches. The angle (A) formed between the inclination of the tool tip and the long axis of the handpiece and connecting member is about 40 degrees and the bevel of the tip end is about 30 degrees. The connecting member is securely attached to the tool tip by brazing, with the tip having an overall length of about 0.87 inches.

It should also be understood that the aforesaid description of the preferred methods for practicing the procedures according to this invention is not exclusive and that the surgeon may utilize the apparatus of this invention in any desired made of operation. For instance the various modes of operation of the aforesaid apparatus are as follows:

The apparatus may be operated in the irrigation mode only, so as to provide a forceful flow of sterile fluid to the surgical site by spraying the fluid from the handpiece irrigation nozzel.

It may be operated in the aspiration mode only so as to allow the surgeon to evacuate excess fluid from the operative site. It may be operated simultaneously in the irrigation and aspiration modes in order to allow cleansing of the operative site while aspirating fragmented tissue and blood. When ultrasonic excitation is applied to the tool tip the apparatus of this invention is operated in the ultrasonic "fragmentation" and aspiration modes simultaneously whereby fragmentation of tissue and aspiration thereof takes place simultaneously. Upon termination of ultrasonic vibration excitation, i.e., fragmentation mode, the aspiration line 60 is automatically vented to atmosphere via vent valve 62 causing instant release of tissue adjacent the tool tip. Also, as aspiration takes place through the vibrating hollow tool tip, the area of tissue being treated at any one time is limited to that defined by the tip itself as opposed to any apparatus requiring aspiration through a tube other than the tool tip. Another important operative mode according to this invention is simultaneous irrigation as well as fragmentation and aspiration which mode is principally employed during fragmentation of tissue.

Having fully described the apparatus and method of our invention and wishing to cover those variations and modifications which would be apparent to one skilled in the art, but without departing from either the spirit or scope thereof,

We claim:

1. Apparatus for removing an exposed layer of soft tissue such as neurological-type tissue, said apparatus comprising:
    a tool tip having a longitudinal axis extending from one end of said tool tip; and
    a connecting member extending from said tool tip for connecting said tool tip to ultrasonic means such that said ultrasonic means ultrasonically vibrates said tool tip flexurally and said one end of said tool tip substantially entirely transversely to said longitudinal axis of said tool tip, whereby said transversely vibrating end of said tool tip can be swept back and forth across said exposed layer of soft tissue in a plane generally parallel to said transverse vibration of said tool tip end to comminute and thereby remove said exposed layer of soft tissue.

2. Apparatus according to claim 1; and additionally comprising:
    irrigation means positioned adjacent said tool tip for supplying fluid to a site adjacent said tool tip, and
    aspiration means also positioned adjacent to said tool tip for withdrawing fluid and suspended, comminuted tissue material from said site adjacent said tool tip at the moment of comminution to thereby maintain clear surgical vision of said swept tissue.

3. The apparatus according to claim 2 wherein said aspiration means has an aspiration vent valve responsively opened when said ultrasonic means is shut off.

4. The apparatus according to claim 1 wherein said connecting member has a longitudinal axis extending from said tool tip to said ultrasonic means and said tool tip end is a plane forming an angle of between 30 degrees and 90 degrees with said longitudinal axis of said connecting member.

5. The apparatus according to claim 1 wherein said tool tip is vibrated in the frequency range of from 20 KHz to 40 KHz with a transverse vibratory amplitude of said end of said tool tip of from about 0.0005 inch to about 0.005 inch peak to peak.

6. The apparatus according to claim 1 wherein said tool tip is vibrated at a frequency of about 25 KHz.

7. The apparatus according to claim 1; wherein said connecting member extends along a longitudinal axis, and said ultrasonic means vibrates said connecting member along its longitudinal axis; and further comprising means for converting said ultrasonic vibration of said connecting member along said longitudinal axis of said connecting member to said substantially entirely transverse vibration of said one end of said tool tip and connecting member.

8. The apparatus according to claim 1; and further comprising said ultrasonic means for ultrasonically vibrating at least said one end of said tool tip substantially entirely transversely to said longitudinal axis of said tool tip.

9. Apparatus for removing an exposed layer of soft tissue such as neurological-type tissue, said apparatus comprising:
    a hollow tool tip having a longitudinal axis extending from one end of said tool tip;
    irrigation and aspiration means for independently irrigating a site on said exposed layer of soft tissue when operatively swept by said end of said tool tip and aspirating said site to withdraw fluid and comminuted tissue mixed therewith whereby better vision of said site is obtained, one of said irrigation and aspiration means comprising said hollow tool tip; and a connecting member having a longitudinal axis extending at an angle from said longitudinal axis of said tool tip for connecting said tool tip to ultrasonic means for ultrasonically vibrating said tool tip flexurally and at least said one end of said tool tip substantially entirely transversely to said longitudinal axis of said tool tip for comminuting said exposed layer of soft tissue when swept by said end of said tool tip.

10. The apparatus according to claim 9; and further comprising said ultrasonic means for ultrasonically vibrating at least said one end of said tool tip substantially entirely transversely to said longitudinal axis of said tool tip.

11. For use in apparatus for removing an exposed layer of tissue such as neurological-type tissue and having ultrasonic means for producing ultrasonic vibrations, a tool comprising:

a tool tip having a longitudinal axis extending from one end of said tool tip; and connecting member means having a longitudinal axis extending from said tool tip for connecting said tool tip to said ultrasonic means such that said ultrasonic means vibrates said connecting member means along said longitudinal axis thereof, said connecting member means cooperating with said tool tip for converting said longitudinal vibrations of said connecting member means into flexural vibrations of said tool tip and, at said end of said tool tip, vibrations substantially entirely transverse to said longitudinal axis of said tool tip, whereby said transversely vibrating end of said tool tip can be swept across said exposed layer of soft tissue in a plane generally parallel to said transverse vibration of said tool tip to comminute and thereby remove said exposed layer.

12. Apparatus as set forth in claim 11; and further comprising said ultrasonic means for producing said ultrasonic vibrations.

* * * * *